(12) United States Patent
Peterson et al.

(10) Patent No.: US 12,036,413 B2
(45) Date of Patent: Jul. 16, 2024

(54) NERVE STIMULATION SYSTEM

(71) Applicant: Galvani Bioelectronics Limited, Stevenage (GB)

(72) Inventors: David Karl Lee Peterson, Wilmington, DE (US); Daniel John Chew, Brentford (GB); Matteo Donega, Brentford (GB); Xu Meng, Wilmington, DE (US)

(73) Assignee: Galvani Bioelectronics Limited, Stevenage (GB)

( * ) Notice: Subject to any disclaimer, the term of this patent is extended or adjusted under 35 U.S.C. 154(b) by 346 days.

(21) Appl. No.: 17/415,599

(22) PCT Filed: Dec. 13, 2019

(86) PCT No.: PCT/IB2019/060771
§ 371 (c)(1),
(2) Date: Jun. 17, 2021

(87) PCT Pub. No.: WO2020/128748
PCT Pub. Date: Jun. 25, 2020

(65) Prior Publication Data
US 2022/0080208 A1    Mar. 17, 2022

Related U.S. Application Data

(60) Provisional application No. 62/782,825, filed on Dec. 20, 2018.

(51) Int. Cl.
*A61N 1/00* (2006.01)
*A61N 1/05* (2006.01)
*A61N 1/36* (2006.01)

(52) U.S. Cl.
CPC ....... *A61N 1/36167* (2013.01); *A61N 1/0551* (2013.01)

(58) Field of Classification Search
CPC .............. A61N 1/36167; A61N 1/0551; A61N 1/0556; A61N 1/36135; A61N 1/36128; A61N 1/36178; A61B 5/4041
See application file for complete search history.

(56) References Cited

U.S. PATENT DOCUMENTS

| 2014/0046407 A1 | 2/2014 | Ben-Ezra et al. |
| 2016/0158551 A1 | 6/2016 | Kent et al. |

FOREIGN PATENT DOCUMENTS

| WO | WO 1997037721 | 10/1997 |
| WO | WO 2017106539 | 6/2017 |

*Primary Examiner* — Scott M. Getzow
(74) *Attorney, Agent, or Firm* — McAndrews, Held & Malloy, Ltd.

(57) ABSTRACT

A system (1) for electrically stimulating a nerve (3), the system comprising: a first stimulator (5) and a second stimulator (7) for electrically stimulating the nerve, the first stimulator and the second stimulator spaced apart from one another by a first distance; and a controller (9) arranged to: a) set a time interval as a function of the first distance and the speed of propagation of an action potential in the nerve; b) activate the first stimulator for a first stimulation period, thus inducing electrical activity in the nerve; and c) activate the second stimulator for a second stimulation period after the time interval has elapsed after the end of the first time period. Preferably, the time interval is a sum of the first time period and a buffer time period for allowing the nerve to recover from stimulation.

18 Claims, 7 Drawing Sheets

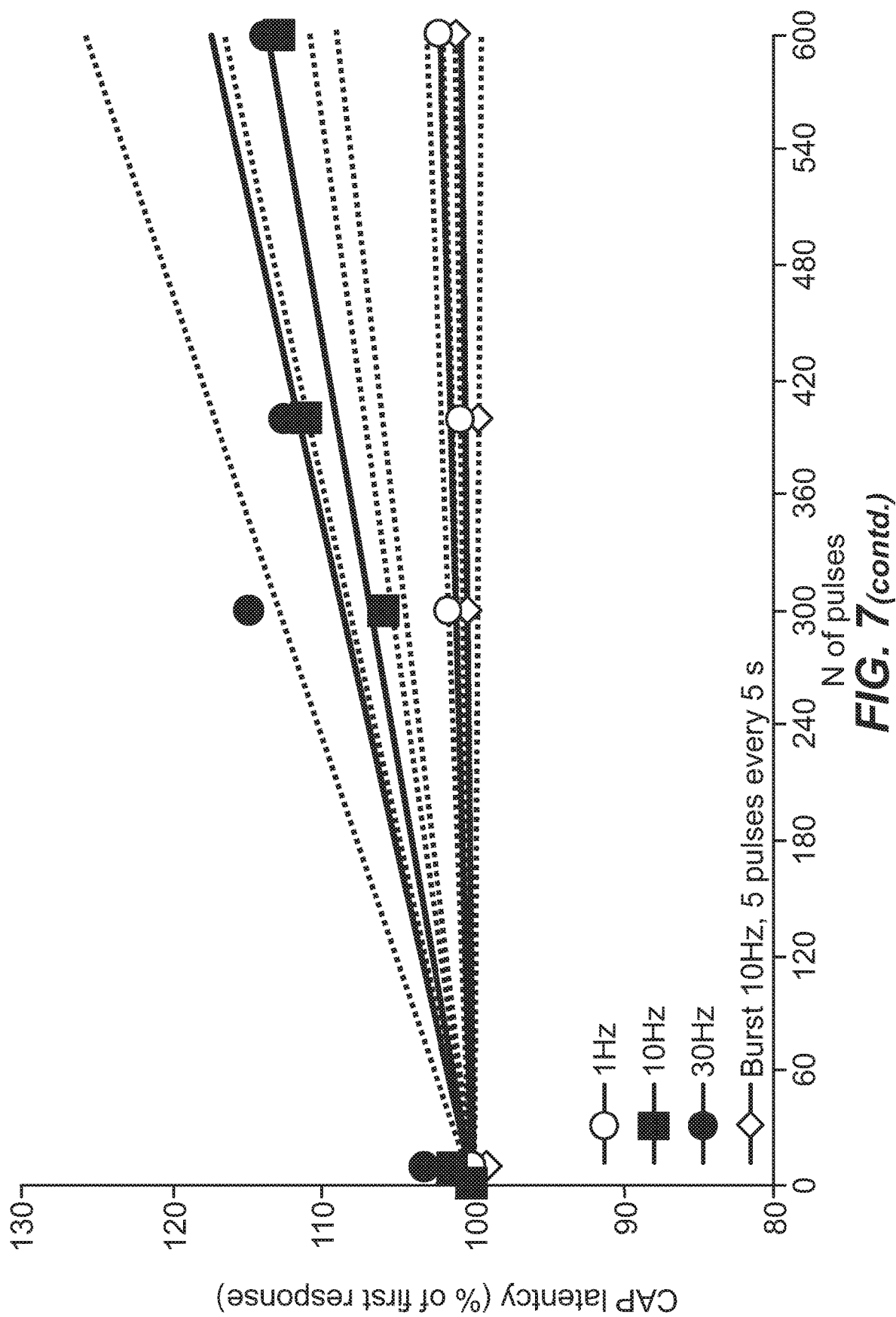
FIG. 7 (contd.)

NERVE STIMULATION SYSTEM

This application is a U.S. National Phase Application under 35 U.S.C. § 371 of International Application PCT/IB2019/060771, filed Dec. 13, 2019 which claims the benefit of U.S. Provisional Application No. 62/782,825, filed on Dec. 20, 2018. Each of these applications is hereby incorporated by reference in its entirety for all purposes.

TECHNICAL FIELD

This disclosure relates to systems and methods for electrically stimulating a nerve.

BACKGROUND

It is desirable to electrically stimulate a nerve in a patient at certain frequencies in treating diseases. However, nerves are susceptible to fatigue (also known as and referred to as action potential conduction slowing, APCS) when stimulated at frequencies above a particular level. For instance, C-fibers, unmyelinated fibers, which make up the nerves in the splenic neurovascular bundle are subject to fatigue, APCS, and become less responsive over time when stimulated at certain frequencies. The reduced responsiveness may be due to the elongated action potential profile of polarization and repolarisation across the membrane (Ringkamp et al. 2010 PLoS ONE 5(2): e9076 doi:1371/journal.pone.0009076).

C-fibers, unmyelinated fibers, require much higher levels of electrical stimulation to activate in comparison to the larger nerve fibers in somatic nerves. This exacerbates the issue of fatigue, APCS. The high activation thresholds also mean that nerve activation takes place close to the electrode contacts where current density and field curvature are the highest. Axon activation takes place first closest to the electrode contacts and axons further from the electrode contacts (for example, those within a fascicle or within an anatomical structure of a neurovascular bundle, are activated later, or may not be activated at all.

Activation thresholds are lower for cathodic pulses (i.e. pulses originating at the cathode) in comparison to anodic pulses (i.e. pulses originating at the anode). This difference in thresholds may be attributed to the polarized resting membrane potential of the axon. However, cathodic pulses can cause anodic block at the contact edges, if the nerve fiber is very close to the cathode contact surface. Anodic block can block action potential propagating away from the contact along the nerve. By contrast, anodic pulses may be more effective in activating fibers that are close to the electrode because depolarisation occurs at the edges of the contact.

Conventional bipolar neural interfaces use the electrode that is closer to the target organ (i.e. the distal contact) exclusively as a cathode and the electrode that is further from the target organ (i.e. the proximal contact) exclusively as an anode. Fibers close to the cathode surface are subject to anodic block at the contact edge. In addition, fibers deeper below the anode contact surface may not be activated due to the higher threshold activation. In addition, the current is limited by the higher compliance voltage needed for a bipolar electrode versus a unipolar electrode. Conventional bipolar stimulation under-utilises the ability of each contact to activate nearby nerve fibers.

Therefore, there is a need for system that electrically stimulates nerve fibers more effectively, for instance by reducing nerve fatigue, APCS, reducing anodic block and allowing deeper nerve fibers to be activated. This new system would produce a greater and more uniformed bolus of axons firing and activating the target structure, and produce a more effective therapy.

SUMMARY

In one aspect of the invention there is a system for electrically stimulating a nerve, the system comprising: a first stimulator and a second stimulator for electrically stimulating the nerve, the first stimulator and the second stimulator spaced apart from one another by a first distance; and a controller arranged to: a) set a time interval as a function of the first distance and the speed of propagation of an action potential in the nerve; b) activate the first stimulator for a first stimulation period, thus inducing electrical activity in the nerve; and c) activate the second stimulator for a second stimulation period after the time interval has elapsed after the end of the first time period.

In this way, the system introduces a delay (i.e. the time interval) between the stimulation applied by the first stimulator and the stimulation applied by the second stimulator. This delay provides time for the nerve to recover (i.e. repolarize) from the first stimulation before the second stimulation is applied. Specifically, the delay is a function of the distance between the stimulators and the speed of propagation of an action potential in the nerve which can be used to set the delay to be greater than the time taken for the stimulation to travel from the first stimulator to the second stimulator. This ensures that the second stimulator does not activate the nerve (or prevent the nerve from further stimulation) while it is still being stimulated at the location of the second stimulator as a result of the first stimulation. For example, the second stimulator does not attempt to activate the nerve while the action potential of the first stimulation is near the location of the second stimulator. In addition, using two stimulators placed at different locations reduces the number of stimulations applied at a particular location, thus reducing nerve fatigue, APCS, at that location.

The time interval may include a first time period that is approximately equal to, or greater than, the first distance divided by the speed of propagation of an action potential in the nerve. In this way, the delay can be equal to or greater than the time taken for the stimulation to travel from the first stimulator to the second stimulator. This ensures that the second stimulator does not activate the nerve while it is still being stimulated at the location of the second stimulator as a result of the first stimulation. For example, the second stimulator does not attempt to active the nerve while the action potential of the first stimulation is near the location of the second stimulator.

In one example, the speed of an action potential in the nerve is around 0.5 mm/ms. This may be the case when the nerve is an autonomic nerve, such as the splenic nerve. In one example, the first distance between the first and second stimulators is approximately equal to, or greater than, 3 mm. When the first distance is approximately equal to, or greater than, 3 mm, the first time period is approximately equal to, or greater than, 6 ms. When the first distance between the first and second stimulators is equal to, or greater than, 5 mm, the first time period is approximately equal to, or greater than, 10 ms. When the first distance between the first and second stimulators is around 6 mm, the first time period is approximately equal to, or greater than, 12 ms. When the first distance is around 6.4 mm, the first time period is approximately equal to, or greater than, 12.8 ms. These parameters ensure that the second stimulator does not activate the nerve while it is still being stimulated at the location of the second stimulator as a result of the first stimulation. For example, the parameters are such that the second stimulator does not attempt to activate the nerve while the action potential as a results of the first stimulation is near the location of the second stimulator.

The time interval may be set as a sum of the first time period and a buffer time period for allowing the nerve to recover from stimulation. This helps to ensure that the nerve has sufficient time to fully recover before the second stimulation is applied. The buffer time period may be equal to, or greater than, the length of time required for the effect of the electrical activity induced in the nerve at the location of the second stimulator to diminish below a predetermined threshold, or to be diminished entirely. For instance, the buffer time period may be equal to, or greater than, 10 ms. This provides a sufficient length of time for autonomic nerve fibres to recover. The electrical activity in the nerve is related to the recovery of sodium channels in the nerve to the point where these channels can be electrically activated again. The end of the buffer time period may be set to be after the relative refractory period of the nerve. This may be when the majority of the sodium channels have recovered to an excitable state.

The time interval is equal to, or less than, half of the first time stimulation period. This is the preferred maximum length of time between the first stimulation and the second stimulation. It is desirable to maximise the time between pulses in order to have the most time possible for the nerve to recover to the most excitable state. In the case of unmyelinated fibers, for example, the C-fibers, being activated, more time for recovery may be required than for other nerves.

Each one of the first and the second stimulators may comprise one or more electrodes. The system may further comprise attachment means for electrically coupling the first and second stimulators to the nerve, wherein the attachment means defines an aperture having an internal diameter for receiving the nerve. The internal diameter may be approximately equal to, or greater than, 5 mm. The internal diameter may be approximately equal to, or less than, 13 mm. The internal diameter may be approximately 7.5 mm.

The system may be attached to the nerve. The system may be attached to a nerve-tissue structure, for example, a neurovascular bundle. The nerve may be an autonomic nerve, such as the splenic nerve of the patient. The nerve may be an unmyelinated nerve.

The system may surround the nerve, for example, the system may partially or fully surround the nerve. The system that surrounds the nerve may attach to the nerve. The system that surrounds the nerve may not attach to the nerve but may be in physical contact with the nerve. The nerve may be an autonomic nerve, such as the splenic nerve of the patient. The nerve may be an unmyelinated nerve.

The controller may be further arranged to: execute step b) after the time interval has elapsed after the end of the second stimulation period. The controller may be further arranged to: repeat steps c) and d) so as to alternately stimulate the first and second stimulators. Therefore, the first and second stimulators can be stimulated alternately and repeatedly. The first stimulation period and the second stimulation period may be approximately equal to one another. This balances the stimulation between the first and second stimulators, thus evening out any fatigue, APCS, effects over the stimulators.

In another aspect of the invention there is a system for electrically stimulating a nerve, the system comprising: a first stimulator for electrically stimulating the nerve at a first stimulation site and a second stimulator for electrically stimulating the nerve at a second stimulation site, the first stimulator and the second stimulator spaced apart from one another by a first distance; a controller arranged to: activate the first stimulator for a first stimulation period, thus inducing electrical activity in the nerve at the first stimulation site and the second stimulation site; and activate the second stimulator, only after the amount of induced electrical activity at the second stimulation site has fallen below a threshold amount of electrical activity.

In another aspect of the invention there is a method of electrically stimulating a nerve, the method comprising: positioning a first stimulator at a first stimulation site of the nerve; positioning a second stimulator at a second stimulation site of the nerve; activating the first stimulator for a first time period, thus inducing electrical activity in the nerve at the first and second stimulation sites; and activating the second stimulator for a second time period, only after the amount of induced electrical activity at the second stimulation site has fallen below a threshold amount of electrical activity.

BRIEF DESCRIPTION OF THE DRAWINGS

Embodiments of the invention will be described, by way of example, with reference to the following drawings, in which.

DETAILED DESCRIPTION

Figure 1:
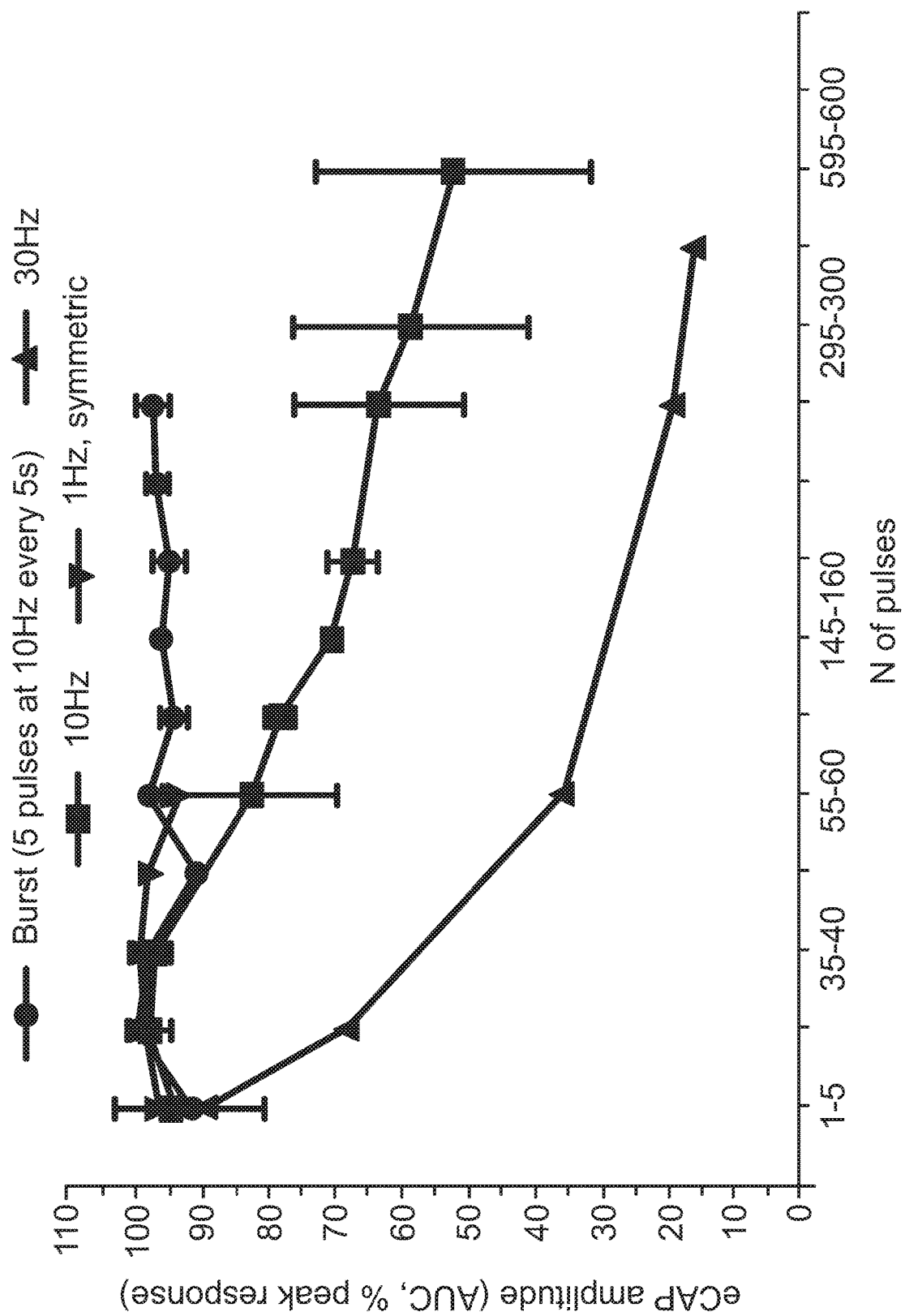
FIG. 1 illustrates how the responsiveness of the splenic nerve varies as a percentage of the peak response with respect to the number of pulses applied to it and to the frequency of the stimulation.

FIG. 1 illustrates how the responsiveness of the splenic nerve, unmyelinated fibers, varies as a percentage of the peak response with respect to the number of pulses applied. As shown in FIG. 1, when the splenic nerve is stimulated at a frequency of 30 Hz the rate of fatigue, APCS, of the nerve is high. A stimulation frequency of 10 Hz causes fatigue, APCS, in the nerve also, but at a less rapid rate. By contrast, stimulating the nerve with a frequency of 1 Hz and stimulating the nerve with 5 pulses at 10 Hz every 5 seconds causes less fatigue, APCS. Stimulating the nerve with a frequency of 1 Hz causes almost no conduction slowing and stimulating the nerve with 5 pulses at 10 Hz every 5 seconds also effectively prevents conduction slowing However, it is undesirable for stimulation to be limited to these frequencies and stimulation patterns. Frequencies between 1 Hz and 10 Hz are desirable.

Unmyelinated fibers show a reduction in conduction velocities when they are subjected to a stimulus preceded by a conditioning stimulus, depending on the delay between the two pulses (the frequency of the stimulation) and also the total number of pulses generated. When recording CAP, this phenomenon manifests as reduction in CAP amplitude and increase in latency, reduction in conduction velocity.

Figure 2:
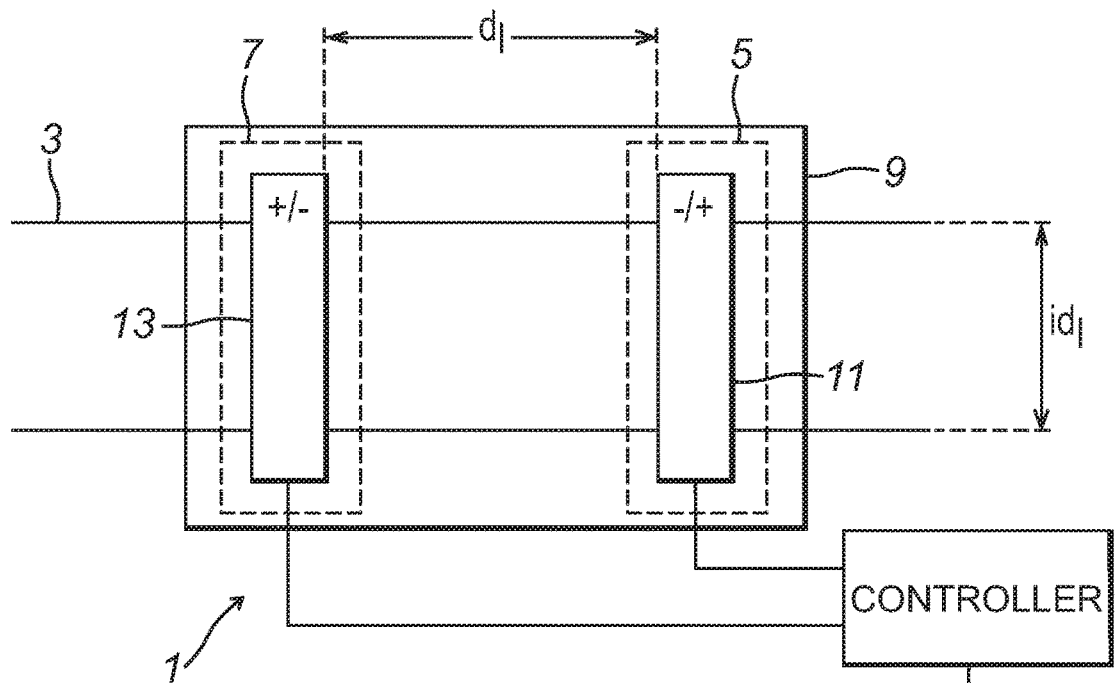
FIG. 2 illustrates an example of a nerve stimulation system.

Referring to FIG. 2, there is a system 1 for electrically stimulating a nerve 3. The system comprises a first stimulator 5 and a second stimulator 7 operatively coupled to a controller 9 that controls stimulations applied by the stimulators 5, 7. The stimulators 5, 7 are attached to a nerve interface 9, such as an electrode cuff. The nerve interface 9 comprises an aperture that has an internal diameter ($id_1$) which is sized to receive the nerve 3. The first stimulator 5 and the second stimulator 7 are separated by a first distance ($d_1$).

The internal diameter ($id_1$) may be approximately equal to, or greater than, 5 mm. The internal diameter ($id_1$) may be approximately equal to, or less than, 13 mm. The internal diameter ($id_1$) may be approximately 7.5 mm. These parameters are preferable for use with the splenic nerve of human subjects.

In the example illustrated in FIG. 2, the first stimulator 5 comprises a first electrode 11 and the second stimulator 7 comprises a second electrode 13. The controller 9 is configured to stimulate the electrodes 11, 13 in order to provide either anodic pulses during which the controller 9 applies a negative current to one of the electrodes or cathodic pulses during which the controller 9 applies a positive current to one of the electrodes.

The controller 9 is arranged to activate the first stimulator 5 in order to provide a first electrical stimulation to the nerve 3 for a first stimulation period. This induces electrical activity in the nerve 3, which may be an action potential in the nerve 3. This electrical activity travels along the nerve between the first stimulator 5 and the second stimulator 7.

The controller 9 is also arranged to activate the second stimulator 7 in order to provide a second stimulation to the nerve 3 for second stimulation period. This induces electrical activity in the nerve 3, which may be an action potential in the nerve. This electrical activity travels along the nerve between the second stimulator 7 and the first stimulator 75

The controller 9 may be configured to operate the first electrode 11 as a cathode and the second electrode 12 as an anode during a first phase. Then, the controller 9 may be configured to operate the first electrode 11 as an anode and the second electrode 13 as a cathode during a second phase. The first and the second phase may be within the same stimulation period.

The controller 9 is arranged to set a time interval that defines a delay between stimulating the first stimulator 5 and the second stimulator 7. This may be preprogramed and/or the controller 9 may be provided with a user interface that allows an operator to set the time interval.

Figure 3:
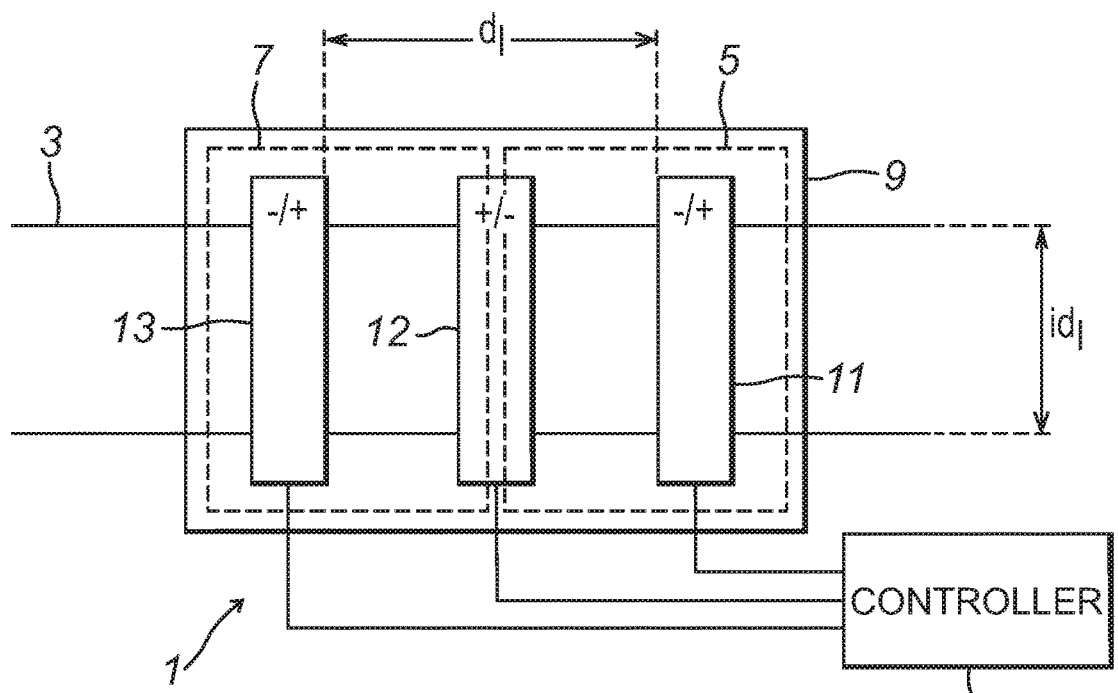
FIG. 3 illustrates another example of a nerve stimulation system.

Referring to FIG. 3, there is a system 1 for electrically stimulating a nerve 3 which is similar to the system 1 described with reference to FIG. 2. In the system 1 illustrated in FIG. 3, the first stimulator 5 comprises the first electrode 11 and a third electrode 12. In addition, the second stimulator 7 comprises the second electrode 13 and the third electrode 12. Thus, the first stimulator 11 and the second stimulator 7 share the third electrode 12.

In an additional embodiment, the third electrode has a larger surface area than the first and second electrodes. The third electrode may, for example, be the IPG case.

The controller 9 is configured to stimulate the electrodes 11, 12, 13 in order to provide either anodic pulses during which the controller 9 applies a negative current to one of the electrodes, or cathodic pulses during which the controller 9 applies a positive current to one of the electrodes.

In a similar manner to that described above, the controller 9 is arranged to activate the first stimulator 5 in order to provide a first electrical stimulation to the nerve 3 for a first stimulation period. In one example, this involves stimulating the first electrode 11 and/or the third electrode 12 in order to provide either an anodic pulse or a cathodic pulse. For an anodic pulse, the controller 9 applies a negative current to either one of the first electrode 11 or the third electrode 12. For a cathodic pulse, the controller 9 applies a positive current to either one of the first electrode 11 or the third electrode 12.

The controller 9 is also arranged to activate the second stimulator 7 in order to provide a second stimulation to the nerve 3 for a second stimulation period. In one example, this involves stimulating the second electrode 13 and the third electrode 12 in order to provide either an anodic pulse or a cathodic pulse. For an anodic pulse, the controller 9 applies a negative current to either one of the second electrode 13 or the third electrode 12. For a cathodic pulse, the controller 9 applies a positive current to either one of the second electrode 13 or the third electrode 12.

The controller 9 may be configured to operate the first electrode 11 and/or the second electrode 13 as a cathode and the third electrode 12 as an anode during a first phase. Then, the controller 9 may be configured to operate the first electrode 11 and/or the second electrode 13 as an anode and the third electrode 12 as a cathode during a second phase. The first and the second phase may be within the same stimulation period.

Figure 4:
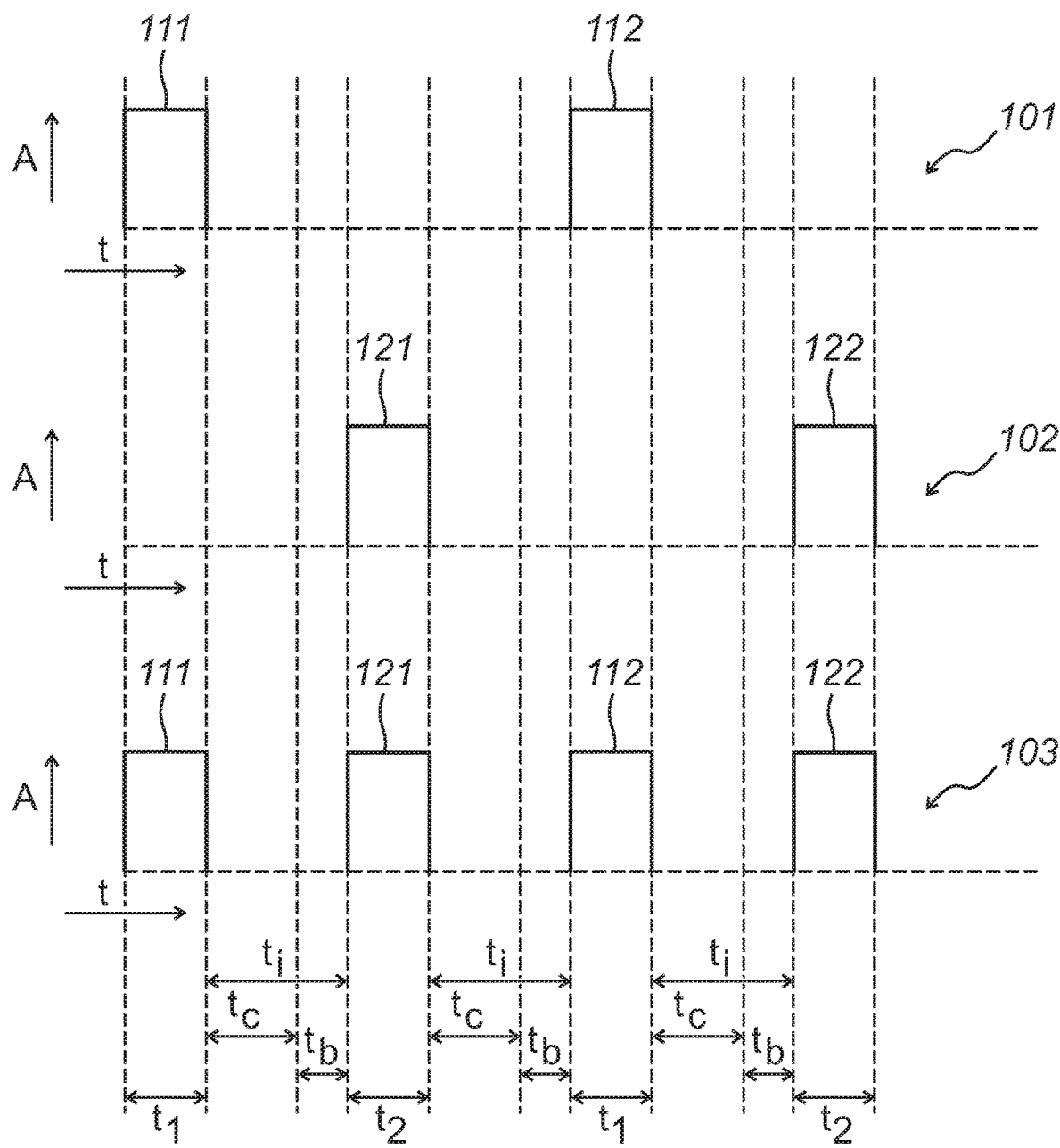
FIG. 4 illustrates an example of a stimulation timing sequence.

FIG. 4 illustrates an example of a timing sequence for the stimulation provided by the system 1 described with reference to FIGS. 2 and 3. There is a first timing sequence 101 that illustrates stimulation provided by the first stimulator 5, a second timing sequence 102 that illustrates stimulation provided by the second stimulator 7, and a combined timing sequence 103 that illustrates the combined effect in the nerve 3 of the stimulations provided by the first and second stimulators 5, 7.

Referring to FIGS. 2 to 4, firstly the first stimulator 5 stimulates the nerve 3 with a first electrical stimulation 111 for a first stimulation time period ($t_1$). Next, the second stimulator 7 stimulates the nerve 3 with a second stimulation 121 for a second stimulation time period ($t_2$). Then, the first stimulator 5 stimulates the nerve 3 with a third electrical stimulation 112 for the first stimulation time period, and after that the second stimulator 7 stimulates the nerve 3 with a fourth stimulation 122 for the second stimulation time period. This process can be repeated so that the first and second stimulators 5, 7 are activated alternately.

In FIG. 4, the stimulations 111, 121, 112, 122 are square wave pulses. However, this is only one example, and different stimulation patterns could you used, such as a burst of pulses and/or biphasic pulses.

As can be seen in FIG. 4, there is a time interval ($t_i$) between the first electrical stimulation 112 and the second electrical stimulation 121. This is the delay between the end of the first stimulation 112 and the beginning of the second stimulation 121.

The time interval ($t_i$) is set in order to ensure that the electrical activity induced by the first stimulation has subsided in the vicinity of the second stimulator before the second stimulation is activated. The delay is set as a function of the distance between the stimulators 5, 7 (i.e. the first distance $d_1$) and the speed of propagation of an action potential in the nerve.

In this example, the time interval ($t_i$) comprises at least one component ($t_c$) (i.e. a first time period) that is defined by a function of the first distance ($d_1$) and the speed of propagation. This function defines that the first time period is approximately equal to, or greater than, the first distance ($d_1$) divided by the speed of propagation of an action potential in the nerve (v). The speed of propagation is the speed at which electrical signals will travel between the stimulators 5, 7. The function may written as follows:

$$t_c \geq d_1/v$$

For instance, the speed of propagation for autonomic nerves, such as the unmyelinated C-fibers in the splenic nerves, is 0.5 mm/ms. The stimulation time periods, $t_1$ and $t_2$, may each be equal to 1 ms.

Therefore, the function may define the first time period as set out in the following table, giving rise to the combined effective stimulation frequency rates shown in Table 1:

TABLE 1

| Propagation Speed (v) | First Distance ($d_1$) | First Time Period ($t_c$) | Stimulation Time Period ($t_1$, $t_2$) | Combined Stimulation Frequency |
| --- | --- | --- | --- | --- |
| 0.5 mm/ms | ≥3 mm | ≥6 ms | 1 ms | ≤142 Hz |
| 0.5 mm/ms | ≥5 mm | ≥10 ms | 1 ms | ≤90 Hz |
| 0.5 mm/ms | ≥6 mm | ≥12 ms | 1 ms | ≤76 Hz |
| 0.5 mm/ms | ~6.4 mm | ≥12.8 ms | 1 ms | ≤72 Hz |

With reference to Table 1, it can be appreciated that the systems allows for higher stimulation frequencies while reducing the issue of fatigue, APCS, in the nerve.

In another this example, the time interval ($t_i$) comprises at least the first time period ($t_c$) defined by the function discussed above and a buffer time period ($t_b$). The time interval ($t_i$) is defined as being greater than, or equal to, the sum of the first time period ($t_c$) and the buffer time period ($t_b$). This function may written as follows:

$$t_i \geq d_1/v + t_b$$

The buffer time period ($t_b$) may be equal to, or greater than, 10 ms. This provides a sufficient length of time for autonomic nerve fibres to recover. However, other time periods could be used depending on the type of nerve. For instance, different fiber types and diameters will have different refractory periods. Myelinated fibers have very short recovery times in the order of a couple milliseconds. Unmyelinated fibers, like C-fibers, need recovery times in the order of 10 ms. The recovery time within a fiber type will be shorter for larger diameters and longer for smaller diameters. Also, increasing the length of the buffer time period ($t_b$) increases the likelihood of the nerve fully recovering before the next stimulation is applied, but reduces the frequency. On the other hand, decreasing the length of the buffer time period ($t_b$) decreases the likelihood of the nerve fully recovering before the next stimulation is applied, but increases the frequency. The buffer time period ($t_b$) can be adjusted in order to find the optimal trade-off between frequency and recovery. An operator can adjust the buffer time period ($t_b$) by interacting with a user interface at the controller 9.

Table 2 shows the time interval ($t_i$) values and the resulting frequency rates when using the propagation speed (v) is 0.5 mm/ms and the stimulation time periods ($t_1$, $t_2$) are each.

TABLE 2

| First Distance ($d_1$) | First Time Period ($t_c$) | Buffer Time Period ($t_b$) | Total Time Interval ($t_i$) | Combined Stimulation Frequency |
| --- | --- | --- | --- | --- |
| ≥3 mm | ≥6 ms | ≥10 ms | ≥16 ms | ≤58 Hz |
| ≥5 mm | ≥10 ms | ≥10 ms | ≥20 ms | ≤47 Hz |
| ≥6 mm | ≥12 ms | ≥10 ms | ≥22 ms | ≤43 Hz |
| ~6.4 mm | ≥12.8 ms | ≥10 ms | ≥22.8 ms | ≤42 Hz |

With reference to Table 2, it can be appreciated that the system allows for high stimulation frequencies while reducing the issue of fatigue, APCS, in the nerve.

Figure 5:
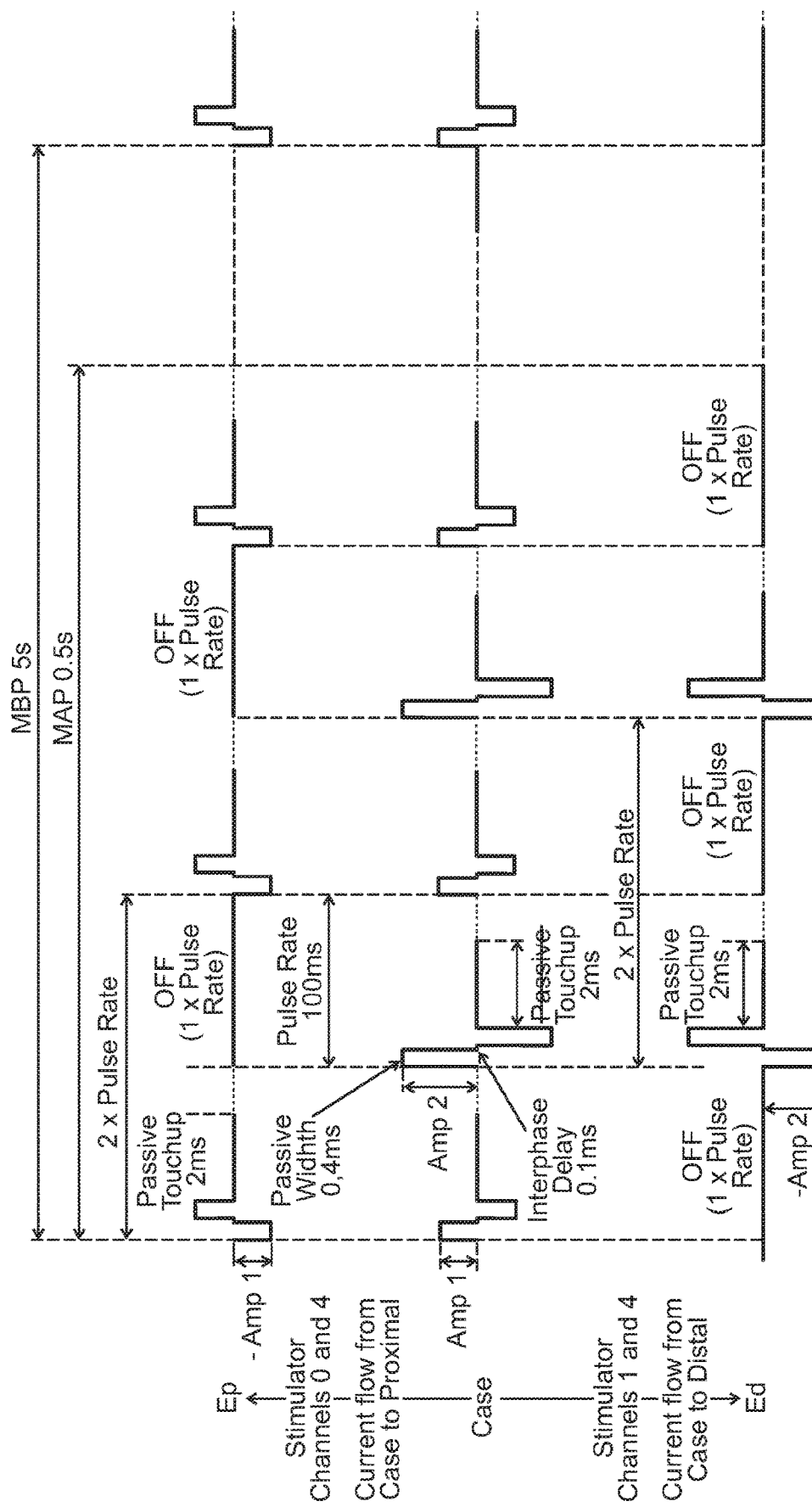
FIG. 5 illustrates another example of a stimulation timing sequence.
Figure 6:
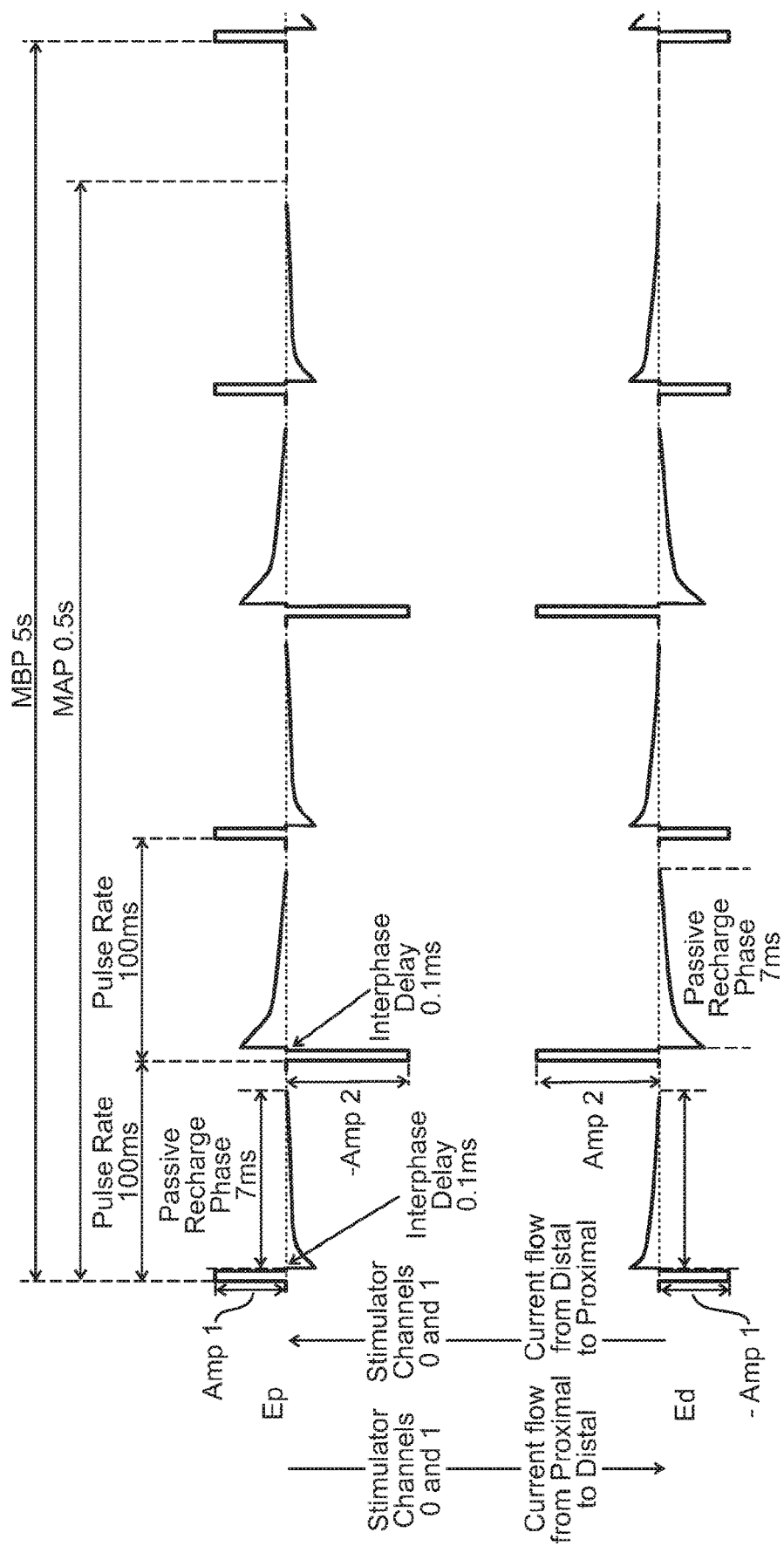
FIG. 6 illustrates a further example of a stimulation timing sequence.
Figure 7:
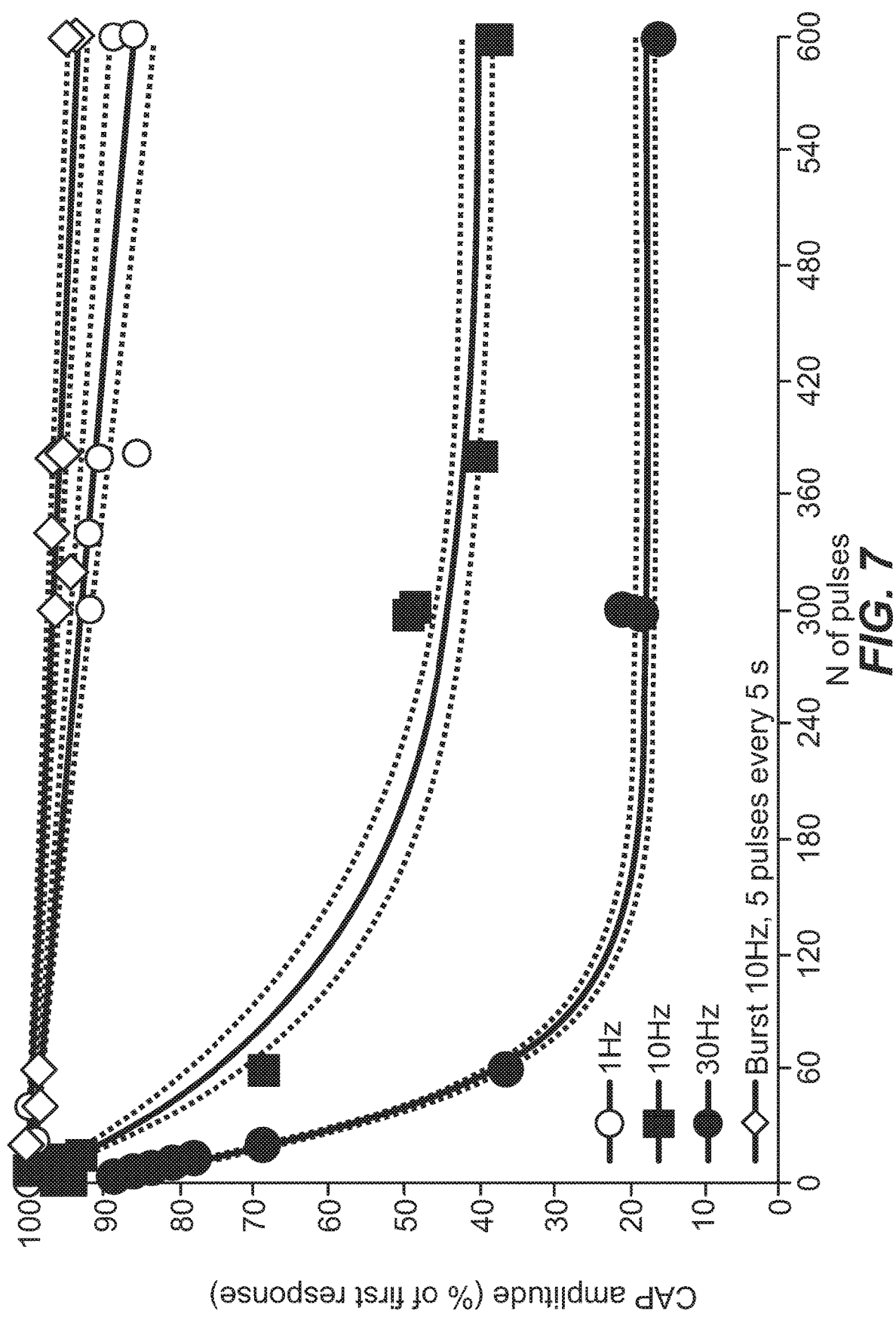
FIG. 7 illustrates the effect of pulse number on the latency (right panel), and therefore conduction velocity, as well as the relative amplitude of the compound action potential (CAP) (left panel) during stimulation of the splenic nerve (unmyelinated axons) at different frequencies.

FIGS. 5 and 6, illustrate specific examples of the simulation patterns provided by the system 1. Referring to FIG. 5, the system 1 alternates the waveform polarity at each stimulator 5, 7 in order to allow anodic activation and cathodic activation. As explained previously, anodic stimulation can activate nerve fibers very close to the contact surface, while cathodic stimulation can activate fibers that are deeper. Thus, it is possible to activate nerve fibers that are both close to and further from the electrodes by using the waveform illustrated in FIG. 5.

FIG. 5 illustrates the current provided by the distal contact ($E_d$), the proximal contact ($E_p$) and the case of a bipolar neural interface. As shown, the neural interface stimulates the nerve with a symmetrical biphasic waveform. In this example, the case always serves as an anode while proximal contact and the distal contact are always cathodes with two distinct timing channels running at the same rate 180° out of phase. Being 180 degrees out of phase means the sequencing interval is one half the interval of the timing channels to maximize the recovery time in the event that a fiber is activated by both contacts.

For a bipolar neural interface with the proximal and distal contact spaced around 6 mm apart from one another along the length of the splenic nerve, an action potential with 0.5 m/s conduction velocity will take ~12 ms to propagate between the contacts. The available recovery time of the nerve is one half of the interval minus ~12 ms, or 38 ms for 10 pps stimulation (i.e. 50 ms sequencing interval). In other words, if it takes 12 ms for the action potential to propagate to the second contact, then the fiber at that second contact has 38 ms to recover after being activated by the passing action potential. The pulse rate at each contact is 10 pps so there is 50 ms after the first contact fires before the second contact fires (50 ms−12 ms=38 ms of recovery time under the second contact). The recovery time (refractory time) for a first stimulated unmyelinated fiber, for example a C-fiber, is under 10 ms. This suggests the burst rate could be up to 30 pps without fatigue, APCS, or exit block if the average pulse rate is ~1 pps. The charge recovery phase of each pulse is delayed by at least 0.1 ms to reduce the activation threshold by avoiding membrane polarization reversal at the activation site before sodium channel activation.

The alternating monopolar stimulation illustrated in FIG. 5 allows all of the stimulator output current to be concentrated on a subset of contacts using the larger surface area of the implantable pulse generator (IPG) case to reduce the required compliance voltage and reduce current density to avoid IPG pocket stimulation.

FIG. 6 illustrates a stimulation pattern that requires four timing channels in order to sequence the proximal contact and the distal contact as anodes and cathodes. This allows fibers very close to the contact surface to be activated be the anodic pulse while deeper fibers are activated by the cathodic pulse. When limited to two timing channels, an alternating bipolar waveform can be used to achieve the same effect as an alternate to monopolar stimulation as shown in FIG. 5.

Passive charge recovery is used in this example as a way to avoid any possible activation by the recharge phase. There is likely no recharge phase activation even with a symmetrical biphasic pulse since reversal of membrane polarization after a sub-threshold primary phase is generally non-excitatory.

The term "comprising" encompasses "including" as well as "consisting" e.g. a composition "comprising" X may consist exclusively of X or may include something additional e.g. X+Y. Unless otherwise indicated each embodiment as described herein may be combined with another embodiment as described herein.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

It will be appreciated that the modules, such as the controller, described herein may be implemented in hardware or in software. Furthermore, the modules may be implemented at various locations throughout the system.

Those skilled in the art will realise that storage devices utilised to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realise that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and a method or apparatus may contain additional blocks or elements.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought. Any of the module described above may be implemented in hardware or software.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of the claims.

The invention claimed is:

1. A system for electrically stimulating a nerve, the system comprising:
   a first stimulator and a second stimulator for electrically stimulating the nerve, wherein each one of the first and the second stimulators comprises one or more electrodes, and the first stimulator and the second stimulator are spaced apart from one another by a first distance; and
   a controller arranged to:
      a) set a time interval as a function of the first distance and a speed of propagation of an action potential in the nerve and a buffer time period, the buffer time period set to allow the nerve to repolarize from a first stimulation period;
      b) activate the first stimulator for the first stimulation period based on the time interval, thus inducing electrical activity in the nerve; and
      c) activate the second stimulator for a second stimulation period after the time interval has elapsed at the end of the first stimulation period.

2. The system of claim 1 wherein the time interval includes a first time period that is approximately equal to, or greater than, the first distance divided by the speed of propagation of the action potential in the nerve.

3. The system of claim 2 wherein the speed of propagation of the action potential in the nerve is around 0.5 mm/ms.

4. The system of claim 2 wherein the first distance between the first and second stimulators is approximately equal to, or greater than, 3 mm, and the first time period is approximately equal to, or greater than, 6 ms.

5. The system of claim 2 wherein the first distance between the first and second stimulators is equal to, or greater than, 5 mm, and the first time period is approximately equal to, or greater than, 10 ms.

6. The system of claim 2 wherein the first distance between the first and second stimulators is around 6 mm, and the first time period is approximately equal to, or greater than, 12 ms.

7. The system of claim 3 wherein the first distance is around 6.4 mm, and the first time period is approximately equal to, or greater than, 12.8 ms.

8. The system of claim 1 wherein the buffer time period is equal to, or greater than, the length of time required for the effect of the electrical activity induced in the nerve at the location of the second stimulator to diminish below a predetermined threshold, or to be diminished entirely.

9. The system of claim 1 wherein the buffer time period is equal to, or greater than, 10 ms.

10. The system of claim 1 wherein time interval is equal to or less than half of the first stimulation period.

11. The system of claim 1 further comprising attachment means for electrically coupling the first and second stimulators to the nerve, wherein the attachment means defines an aperture having an internal diameter for receiving the nerve.

12. The system of claim 11 wherein the internal diameter is approximately equal to, or greater than, 5 mm; or approximately equal to, or less than, 13 mm.

13. The system of claim 1 wherein the nerve is an autonomic nerve.

14. The system of claim 1 wherein the controller is further arranged to:
repeat steps b) and c) so as to alternately stimulate the first and second stimulators.

15. The system of claim 1 wherein the first stimulation period and the second stimulation period are approximately equal to one another.

16. The system of claim 1 wherein the system comprises a third electrode, wherein the third electrode has a larger surface area than either a first and a second electrodes, further wherein the third electrode is an implantable pulse generator case.

17. A system for electrically stimulating a nerve, the system comprising:
a first stimulator for electrically stimulating the nerve at a first stimulation site and a second stimulator for electrically stimulating the nerve at a second stimulation site, the first stimulator and the second stimulator being spaced apart from one another by a first distance;
a controller arranged to:
activate the first stimulator for a first stimulation period, the first stimulation period including a buffer time period to allow the nerve set to repolarize from a first stimulation period, for inducing electrical activity in the nerve at the first stimulation site and the second stimulation site; and
activate the second stimulator, only after the amount of induced electrical activity at the second stimulation site has fallen below a threshold amount of electrical activity.

18. A method of electrically stimulating a nerve, the method comprising:
positioning a first stimulator at a first stimulation site of the nerve;
positioning a second stimulator at a second stimulation site of the nerve;
activating the first stimulator for a first time period, the first time period including a buffer time period set to allow the nerve to repolarize from a first stimulation period, for inducing electrical activity in the nerve at the first and second stimulation sites; and
activating the second stimulator for a second time period, only after the amount of induced electrical activity at the second stimulation site has fallen below a threshold amount of electrical activity.

* * * * *